(12) United States Patent
Petyaev (10) Patent No.: US 7,713,747 B2
(45) Date of Patent: May 11, 2010

(54) METHOD OF ASSESSING RISK OF ATHEROSCLEROSIS

(76) Inventor: Ivan Mikhailovich Petyaev, 126 Walpole Road, Cambridge, CB1 3UE (GB)

( * ) Notice: Subject to any disclaimer, the term of this patent is extended or adjusted under 35 U.S.C. 154(b) by 181 days.

(21) Appl. No.: 10/468,073

(22) PCT Filed: Feb. 15, 2002

(86) PCT No.: PCT/GB02/00694

§ 371 (c)(1),
(2), (4) Date: Dec. 23, 2003

(87) PCT Pub. No.: WO02/065137

PCT Pub. Date: Aug. 22, 2002

(65) Prior Publication Data

US 2004/0137542 A1    Jul. 15, 2004

(30) Foreign Application Priority Data

Feb. 15, 2001    (GB) ................................. 0103766.2

(51) Int. Cl.
*G01N 33/543* (2006.01)

(52) U.S. Cl. ...................... 436/518; 435/7.1; 435/7.92; 435/7.94; 436/501; 436/523

(58) Field of Classification Search ......... 436/506–507, 436/71, 518, 828, 536, 538, 174, 177, 524–526; 435/4, 7.1, 7.92, 174–182, 975; 424/810; 604/5.03

See application file for complete search history.

(56) References Cited

U.S. PATENT DOCUMENTS

| | | | | |
|---|---|---|---|---|
| 4,018,886 A | * | 4/1977 | Giaever | 436/526 |
| 4,332,783 A | * | 6/1982 | Pernice et al. | 435/7.25 |
| 5,900,359 A | * | 5/1999 | Matsuura et al. | 435/7.1 |
| 5,985,578 A | * | 11/1999 | Pestronk | 435/7.1 |
| 6,264,623 B1 | * | 7/2001 | Strahilevitz | 604/5.01 |
| 6,759,385 B1 | * | 7/2004 | Conti-Fine | 514/2 |

OTHER PUBLICATIONS

Mironova M, et al. Anti-modified LDL antibodies and LDL-containing immune complexes in IDDM patients and healthy controls. Clin. Immunol. Immunopathol. 1997;85:73-82.*
Orekhov et al., "Diagnostic Value of Immune Cholesterol as a Marker for Atherosclerosis," Journal of Cardiovascular Risk, vol. 2, No. 5, pp. 459-466 England, Oct. 1995.
Orekhov et al., "Lipoprotein Immune Complexes as Markers of Atherosclerosis ," International Journal of Tissue Reactions, vol. 13, No. 5, 1991, pp. 233-236.
Petyaev et al., "Subsequent use of Protein A and Protein L for the Study of the Content, Distribution and Composition of Anti-Lipoprotein Immune Complexes in Patients with Atherosclerosis," Journal of Submicroscopic Cytology and Pathology, vol. 32, No. 3, Jul. 2000, Abstract Only.
Kalenich et al., "The Cholesterol Content in Immune Complexes as a Marker of Coronary and Peripheral Atherosclerosis,"Database Medline xp002232483, Abstract Only.
Kalenich et al., "Circulating Immune Complex Cholesterol as a Biochemical Marker of Coronary Atherosclerosis," Database Medline XP002232484, Abstract Only.
Tertov et al., "Correlation Between Cholesterol Content in Circulating Immune Complexes and Atherogenic Properties of CHD Patients' Serum Manifested in Cell Culture," Atherosclerosis, vol. 81, No. 3, 1990, pp. 183-190.
Tertov et al., "Low Density Lipoprotein-Containing Circulating Immune Complexes and Coronary Atherosclerosis," Experimental and Molecular Pathology, vol. 52, No. 3, 1990, pp. 300-308.
Klimov et al. "Accumulation of cholesteryl esters in macrophages incubated with human lipoprotein-antibody autoimmune complex" Atherosclerosis 74:41-46 (1988).

* cited by examiner

*Primary Examiner*—Bao-Thuy L Nguyen
*Assistant Examiner*—Gary W Counts
(74) *Attorney, Agent, or Firm*—Nixon & Vanderhye P.C.

(57) ABSTRACT

The invention relates to a method of assessing the risk of suffering from atherosclerosis in an individual comprising removing anti-lipoprotein immune complexes from a sample from the individual, measuring the level of cholesterol/lipoprotein associated with said anti-lipoprotein immune complexes, and determining thereby the risk of atherosclerosis in the individual.

6 Claims, 3 Drawing Sheets

METHOD OF ASSESSING RISK OF ATHEROSCLEROSIS

This application is the U.S. national phase of international application PCT/gb02/00694, filed Feb. 15, 2002, which designated the U.S.

FIELD OF THE INVENTION

The invention relates to a method for determining the risk of an individual suffering from atherosclerosis and in particular suffering from clinical complications of atherosclerosis.

BACKGROUND OF THE INVENTION

Atherosclerosis is a disease which results in narrowed arteries and decreased blood flow. The arteries become narrowed because of a build up of plaques in their inner walls. Plaques consist of a mixture of substances including cholesterol, fat, fibrous tissue, clumps of platelets and sometimes calcium.

Atherosclerosis begins early in life, but generally causes no symptoms until middle or old age. This is because it takes many years for plaques to develop and because normal arteries are much larger than they need to be. Only after an artery becomes very narrowed will blood flow be diminished enough to cause symptoms. When atherosclerosis affects arteries supplying blood to the heart, patients experience angina and claudication.

The formation of lipoprotein-antibody auto immune complexes is associated with lesion development in arteries. These complexes have also been detected in the blood of rabbits with experimental hypercholesterolemia and also in the blood and aorta wall of ischaemic heart disease patients.

Hyperlipidaemia is a risk factor of atherosclerosis. In general, individuals with an increased level of cholesterol are prone to develop or have already developed atherosclerosis. However, although some individuals may not have an increased level of cholesterol, it does not necessarily mean that they do not suffer from atherosclerosis. Hyperlipidaemia has little diagnositic value in cardiovascular pathology since only 10-20% of the total patients with clinical complications of atherosclerosis demonstrate an elevated level of cholesterol in their plasma

SUMMARY OF THE INVENTION

We now provide a simple method for determining the likelihood of an individual suffering from atherosclerosis and in particular from suffering from the clinical complications of atherosclerosis.

In accordance with the present invention, there is provided a method of assessing the risk of an individual of suffering from atherosclerosis, or a clinical complication of atherosclerosis, wherein the method comprises a) removing immune complexes from a sample from the individual;
b) measuring the level of cholesterol/lipoprotein in the treated sample from step (a);
c) determining thereby the risk of atherosclerosis in the individual.

In a particularly preferred aspect of the invention, the immune complexes, that is anti-lipoprotein immune complexes are IgG-based immune complexes. Such complexes may be removed by contacting the sample with an immunoglobulin binding protein like protein A, for example, bound to a solid support. In a particularly preferred aspect of the present invention, protein A is bound to beads. Step (a) comprises incubating the sample with protein A bound to beads and subsequently centrifuging or filtering the sample so treated and collecting the supernatant for the measurement step (b).

DETAILED DESCRIPTION OF THE INVENTION

The present invention makes use of anti-lipoprotein immune complexes comprising antibodies and lipoprotein and monitors the levels of these immune complexes as a marker for atherosclerosis. The method may be used to assist in monitoring atherosclerosis that has already been diagnosed, for example to assess the risk of such an individual from suffering from clinical complications of atherosclerosis. Alternatively, the method may be used as part of the assessment of an individual who has not previously been diagnosed as suffering from atherosclerosis, for example in pre-clinical screening of patients who are not showing clinical complications. The assay may be particularly useful in monitoring patients who have undergone vascular surgery, for example, a heart by pass operation. Restenosis of the graft is accelerated by atherosclerotic occlusion in such patients.

The assay of the present invention may also be used to monitor the effect of treatments or prophylaxis of patients suffering from atherosclerosis or at risk of atherosclerosis by providing a marker for such atherosclerosis and the onset of clinical complications of atherosclerosis.

In particular, the invention provides an indication of cholesterol or lipoprotein associated with immunoglobulin based anti-lipoprotein immune complexes as a marker for atherosclerosis.

In accordance with the method of the present invention, a sample from an individual is treated to remove lipoprotein-antibody complexes from the sample. The levels of cholesterol or lipoprotein associated with these complexes is determined to allow an assessment of the risk of atherosclerosis in the individual. In a preferred aspect of the present invention, the sample taken from the patient is a blood sample. Preferably, the method is carried out on a plasma or serum sample from the patient. Most preferably, the sample is a plasma sample.

Antilipoprotein-immune complexes may be removed from the sample by any suitable method. In a preferred aspect, these complexes are removed from the sample by affinity chromatography using an antibody-binding reagent. Such a reagent will remove all antibodies present in the sample including free antibody and antibody associated with lipoprotein in the anti-lipoprotein immune complexes. Measurement of the levels of cholesterol/lipoprotein associated with the bound antibody fraction provide an indication of cholesterol/lipoprotein associated with anti-lipoprotein immune complexes and hence a marker for atherosclerosis. In a preferred aspect of the present invention, these immune complexes are removed using an antibody sorbent.

Any suitable antibody sorbent may be used. Examples include protein A, protein L, protein G and hybrid proteins based on these proteins such as protein LA. In a preferred aspect, the antibody sorbent for use in connection with the invention binds to immunoglobulin G. In a particularly preferred embodiment, an immunoglobulin G binding domain of protein A is used as the antibody sorbent. Protein A has been well characterised and binds to the Fc portion of IgG. In accordance with the present invention, protein A may comprise whole protein A isolated from Staphylococcus. Alternatively, protein A may comprise recombinant protein A. Fragments of protein A may also be provided, such fragments incorporating at least an IgG binding domain of protein A. Such fragments may comprise homologues or variants of protein A or may form hybrid proteins with other proteins, either as carriers or with other immunoglobulin binding proteins.

The antibody sorbent can be attached to a solid phase. The sample taken from a patient can-be contacted with this antibody sorbent and the anti-lipoprotein complexes thus absorbed onto the antibody sorbent bound to solid phase and removed from the sample.

In a particularly preferred aspect of the invention, the antibody sorbent is provided bound to beads, and in particular to agarose beads.

The antibody sorbent may be bound to the solid support, such as beads using any suitable method. The protein bound to the solid support may be provided as fusion proteins with other proteins either to assist in attachment to the solid support or to provide other functional characteristics which might be desired. The antibody sorbent may be derivatised to assist in its attachment to the solid support such as beads. Linkers may be provided and standard coupling or conjugating techniques used.

Once a sample has been contacted with antibody sorbent bound to a solid support, the levels of lipoproteins/cholesterol associated with the immune complexes may be measured. This may be carried out by any suitable method. The anti-lipoprotein immune complexes bound to the solid support may be separated from the remainder of the sample. This may be carried out in a number of different ways. For example, the antibody sorbent can be supplied as a column through which the sample is passed. Thus, unbound portion of the sample may be collected at the bottom of the column leaving the anti-lipoprotein immune complexes bound to the column via the antibody sorbent. In an alternative and preferred aspect of the invention, the sample is incubated with beads to which the antibody sorbent is bound. These beads may be separated out from the remainder of the sample by centrifugation, filtration or other means such as application of a magnetic field when magnetic beads are used. For example, the sample could be passed through a non-sticky filter which does not retain free lipoproteins/cholesterol in the sample but will retain the antibody-sorbent bound to beads. Alternatively, a magnetic field could be applied to draw magnetic beads with bound anti-lipoprotein immune complexes from the rest of the sample.

In a preferred aspect of the invention, the separation is carried out by centrifugation of the sample so that the supernatant comprising the unbound fraction of the sample can be collected. Alternatively, the beaded antibody-sorbent fraction could be collected from such centrifuged sample.

Preferably, the antibody sorbent is present in sufficient quantity to absorb all antibody from the sample, and preferably an excess of antibody sorbent is contacted with a sample containing antibody. Suitable amounts of antibody sorbent can readily be determined, for example by increasing the amount of antibody sorbent contacted with a sample until no further antibody is removed from the sample.

The cholesterol content or lipoprotein content may be measured by any suitable means. In particular, the total content of cholesterol, apo A-1, B, E or any other parameter of lipoprotein could be determined. For example, triglycerides can be measured by enzymatic colorimetric assays. Apoprotein components can be measured by ELISA, immunoturbidimetric or radioimmunoassays. Suitable kits for measurement of apolipoprotein and triglycerides are readily available and any such assay might be used. An example of a suitable cholesterol assay is available from SIGMA DIAGNOSTICS. Cholesterol esters are first hydrolyzed by cholesterol esterase to cholesterol. The cholesterol produced by hydrolysis is oxidized by cholesterol oxidase to cholest-4-en-3-one and hydrogen peroxide. The hydrogen peroxide can then be coupled with a chromogen in the presence of peroxidase. For example, a quinoneimine dye may be used. The intensity of the colour produced will be directly proportional to the cholesterol concentration in the sample.

In a preferred aspect of the present invention, the cholesterol or lipoprotein content of the sample is measured prior to incubation with the antibody-sorbent. After contact with the antibody-sorbent, the cholesterol or lipoprotein content of the remaining sample so treated is then measured again. A comparison between the cholesterol/lipoprotein levels before and after the treatment provides an indication of the levels of cholesterol/lipoprotein associated with immune complexes and thus provides a marker of athlerosclerotic disease in the individual. Preferably, repeat measurements of cholesterol/lipoprotein levels are carried out using the same measurement technique used to assess those levels prior to treatment.

The levels of cholesterol/lipoprotein measured in accordance with the method may be used in a number of different ways. For example, the level measured in the sample after removal of the anti-lipoprotein immune complexes, or associated with such immune complexes may be compared directly with the levels seen in a healthy individual or an individual known to be suffering from atherosclerosis or the clinical complications of atherosclerosis in order to assess the risk of the individual from suffering from atherosclerosis.

The levels of cholesterol/lipoprotein measured before and after incubation with protein A provide an indication of the levels of cholesterol/lipoprotein associated with anti-lipoprotein antibody immune complexes. The reduction in cholesterol/lipoprotein levels is associated with the amount of cholesterol/lipoprotein associated with anti-lipoprotein immune complexes. The level of this reduction can be compared to samples taken previously from patients known to be suffering from atherosclerosis or showing clinical complications of atherosclerosis. Alternatively, comparison may be made with healthy individuals who do not display atherosclerosis or any of the clinical complications of atherosclerosis. Such comparison provides an indication of the risk of an individual suffering from atherosclerosis and/or from suffering from a clinical complication of atherosclerosis.

Alternatively, a number of samples may be taken from the same individual over a period of time, for example, during the course of a treatment or prophylaxis for atherosclerosis or at monthly or yearly intervals to monitor the progress of that individual and thus provide an indication of the risk or atherosclerosis and clinical complications of atherosclerosis.

In other aspects of the present invention, the method may involve taking repeated samples from the same individual over a period of time and monitoring for changes in the levels of cholesterol or lipoprotein associated with immune complexes to determine alterations in the level of cholesterol/ lipoprotein associated with immune complexes and in particular with IgG to monitor any changes in the risk of that individual from suffering from atherosclerosis or die clinical complications of atherosclerosis.

In another aspect, the invention relates to a kit for use in accordance with the method of the invention.

In particular, a kit in accordance with the present invention comprises means for measuring cholesterol or lipoprotein in a sample and, antibody sorbent, such as protein A bound to a solid support. In a preferred aspect of the invention, the kit comprises antibody sorbent, such as an immunoglobulin binding domain of protein A bound to beads.

EXAMPLES

Materials and Methods

Most of the chemicals were from "SIGMA". rProtein L was from "ACTIGEN". All solutions were prepared in 0.05 M phosphate buffer with 0.1 mM diethylenetriaminepentaacetic acid (DTPA), pH 7.4 unless otherwise stated. All measurements were performed in triplicate at least.

Human specimens. There were two groups of specimens of aorta from patients with clinical complications of atherosclerosis. The first was obtained from necropsy on 21 patients (age range 48-85 years, 16 male, 5 female) at Addenbrooke's Hospital in Cambridge, UK. In some cases more than one lesion samples was taken from the same patient. The pieces of aorta were digested by collagenase.

The second group of specimens together with samples of plasma, serum and in some cases biopsy of quadriceps femoris muscle were recovered from 11 patients (age range 53-64 years, 8 male, 3 female) during bypass surgery of the patients with an abdominal aorta stenosis at the Centre of Cardio-Vascular Surgery of the Clinical Hospital No. 1 in Rostov-na-Donu, Russia. After recovery these samples were immediately put in 30% w/v solution of NaCl and stored at 0-4° C. for 1-2 weeks prior to examination. In the control experiments it was shown that during this period the activities of enzymes such as trypsin, catalase, superoxide dismutase, glutathione peroxidase, creatine kinase and lactate dehydrogenase, together with a level of immunoglobulin (IgG) fragmentation and a degree of lipid peroxidation (concentration of malonaldehydes) did not significantly change (data not presented).

The pieces of aorta (approximately 200-400 mg wet weight) were immersed in phosphate-buffered saline (PBS) and scraped with a blunt glass rod about 8-10 times. Subsequently no further protein could be detected in these extracts. The remaining samples were cut into about ten to twenty pieces each, placed in 5.0 ml of PBS and homogenised by a mechanical homogeniser (ULTRA-TURRAX) at full-power with a 15 mm probe three times for 3 seconds each with 20 second cooling intervals. In order to determine the optimum condition for the extraction of immunoglobulins (Igs) this procedure was performed with different concentrations of two non-ionic detergents, TRITON X-100 and IGEPAL CA-630. After homogenisation the insoluble components were separated by centrifugation at 5000 g for 10 minutes and supernatants were used for analysis.

Immunoglobulin/immune complex extraction. The first step was the treatment of the analysed samples with protein A attached to cross-linked 4% beaded agarose at 37° C. for 30 minutes. After that immunoglobulins and/or immune complexes which had bound via protein A to the beads were spun down at 5000 g for 10 minutes. Supernatants were removed for further tests. Sediments were re-suspended in PBS and the samples were centrifuged again under the same regime. This washing procedure was repeated three times.

In the second step the supernatants were treated with rProtein L attached to cross-linked 4% agarose under the same conditions as described for protein A. The different ratios between proteins A/L and analysed types of material were tested to find the optimal which gives the maximum yield of immunoglobulins (see results).

In the control experiments, instead of protein A reagent, under the same conditions two 10% w/v suspensions of *Staphylococcus aureus* were used; one bearing protein A, Cowan strain, and the other not bearing protein A, Wood 46 strain.

Immunoglobulin content and quantification. Since neither protein A nor rProtein L reagents affect alkaline phosphatase, APase, reaction themselves (data not shown), it was possible to use APase antibody conjugates for immuno-enzyme assays to measure the concentration of immunoglobulins attached to the protein A/L agarose beads. To determine IgG, IgA and IgM anti-human affinity isolated goat antibody APase-conjugates were applied. To determine subclasses of IgG appropriate mouse monoclonal antibodies (IgG class) were firstly used with the subsequent application in the second stage of anti-mouse goat antibody APase-conjugates. The monoclonal anti-human IgG1 was derived from clone SG-16 mouse ascites fluid, anti-human IgG2 from clone HP-6014, anti-human IgG3 from clone HP-6047, anti-human IgG4 from SK-44. The titer of the working solutions for mouse antibodies against IgG1 was 1:2,000, against IgG2 and IgG4 was 1:1,000 and against IgG3 was 1:500. All these antibodies belonged to the mouse IgG1 isotype. The goat conjugates used were pre-absorbed with bovine and human proteins and used in the titer of 1:10,000.

To exclude the binding of these antibodies directly with protein A/L and goat APase conjugates with protein A all analysed samples were preliminarily incubated with bovine IgG in the ratio 2.5 mg of the immunoglobulin per 0.1 ml of the sorbent. The APase conjugates had no cross-reactivity with bovine IgG. Although the binding of these conjugates to rProtein L was much lower than to protein A, the level of this binding, either in the direct or non-direct method, was always measured in control experiments and deducted when the level of immunoglobulins was calculated in the analysed samples.

In order to determine the quantity of immunoglobulins attached to the sorbent the titration of commercial human IgG, IgA and IgM with protein A and rProtein L was performed under the same conditions as for the tested specimens.

Each stage of incubation of the protein A/L extracts with the appropriate antibodies lasted 30 minutes at 37° C., accompanied by centrifugation of the samples at 5,000 g for 10 minutes and their re-suspension in PBS three times. To determine the amount of APase conjugate attached to the sorbent, p-Nitrophenyl Phosphate (pNPP), was used as a substrate for alkaline phosphatase. This substrate was added directly to the beaded conjugate, mixed well and incubated at ambient temperature for 60 minutes. After that all samples were centrifuged for 10 minutes at 5,000 g, supernatants were collected and analysed at $\lambda 400$ nm. In some cases the analysed samples were further diluted in order to make the level of their absorption between 0.03 and 1.0 where it has a lineal character.

'Matched pair' clinical trial. Samples of serum for this trial were collected from 23 patients admitted for bypass cardiovascular surgery with a history of myocardial infarction without any signs of other serious diseases such as diabetes, rheumatoid arthritis, or cancer. This group comprised 20 male and 3 female patients aged between 40 and 60 years. The control group had the same number of clinically healthy men and women with the same profile in age, habits (smoking, drinking) and body constitution.

For the routine analysis in the clinical trial 2 volumes of a sample of serum were mixed with 3 volumes of the suspension of protein A reagent, which provided an excess of this sorbent above any potential level of IgG in the sample. This mixture was then incubated for 30 minutes at 37° C. subsequently centrifuged at 5000 g for 10 minutes. After that one volume of the supernatant was mixed with an equal volume of protein L reagent and treated in the same fashion as described in the previous stage.

An initial sample of serum and the supernatants after its protein A treatment were analysed for protein and total cholesterol content. The difference in the protein content was considered as the amount of IgG attached to protein A. The difference in the cholesterol content reflected the amount of serum lipoproteins associated with these immunoglobulins and was considered as a quantitative measure for anti-lipoprotein immune complexes of IgG (ALICs-IgG).

Immunoglobulin/immune complexes elution from protein A/L reagents. Immunoglobulins (free or in a form of immune complexes) attached to either protein A or rProtein L were delipidated by 5% of Igepal CA-630. After 5 times washing in PBS and centrifuging at 5,000 g for 10 minutes these samples were re-suspended again and incubated in 0.01M acetate buffer pH 2.5 for 30 minutes. Apparently this procedure affects neither covalently bound protein A nor rProtein L to agarose. After a further centrifugation under the same regime, supernatants containing immunoglobulins and, perhaps, their antigens were collected and pH was restored to 7.4.

Protein and cholesterol concentrations. Protein concentration of the extracts was determined by Peterson's modification of the micro-Lowry method, which utilizes sodium dodecylsulfate to facilitate the dissolution of relatively insoluble lipoproteins. Bovine serum albumin was used for the calibration curve.

Cholesterol concentration was determined by an enzymatic assay which couples cholesterol esterase with 4-aminoantipyrine/p-hydroxybenzene-sulfonate/ peroxidase reaction (Sigma kit). To make a calibrating curve a solution of Cholesterol Calibrator was used, which had been certified according to the recommendations of the Centre for Disease Control and the National Cholesterol Education Program, Laboratory Standardization Panel. Since both protein A and rProtein L reagents are indifferent to this assay (data not presented) it was possible, therefore, to measure the level of cholesterol directly associated with these beads. Immune complexes attached to protein A or rProtein L, and containing lipoproteins as their antigen, were mixed well and incubated with a reaction mixture for the enzymatic assay for about 40 minutes at ambient temperature. After that the samples were centrifuged for 10 minutes at 5,000 g, supernatants were collected and analysed at λ520 nm.

Results

Example 1

Extraction of Anti-Lipoprotein Immune Complexes (ALICs) from Plasma/Serum

Figure 1:
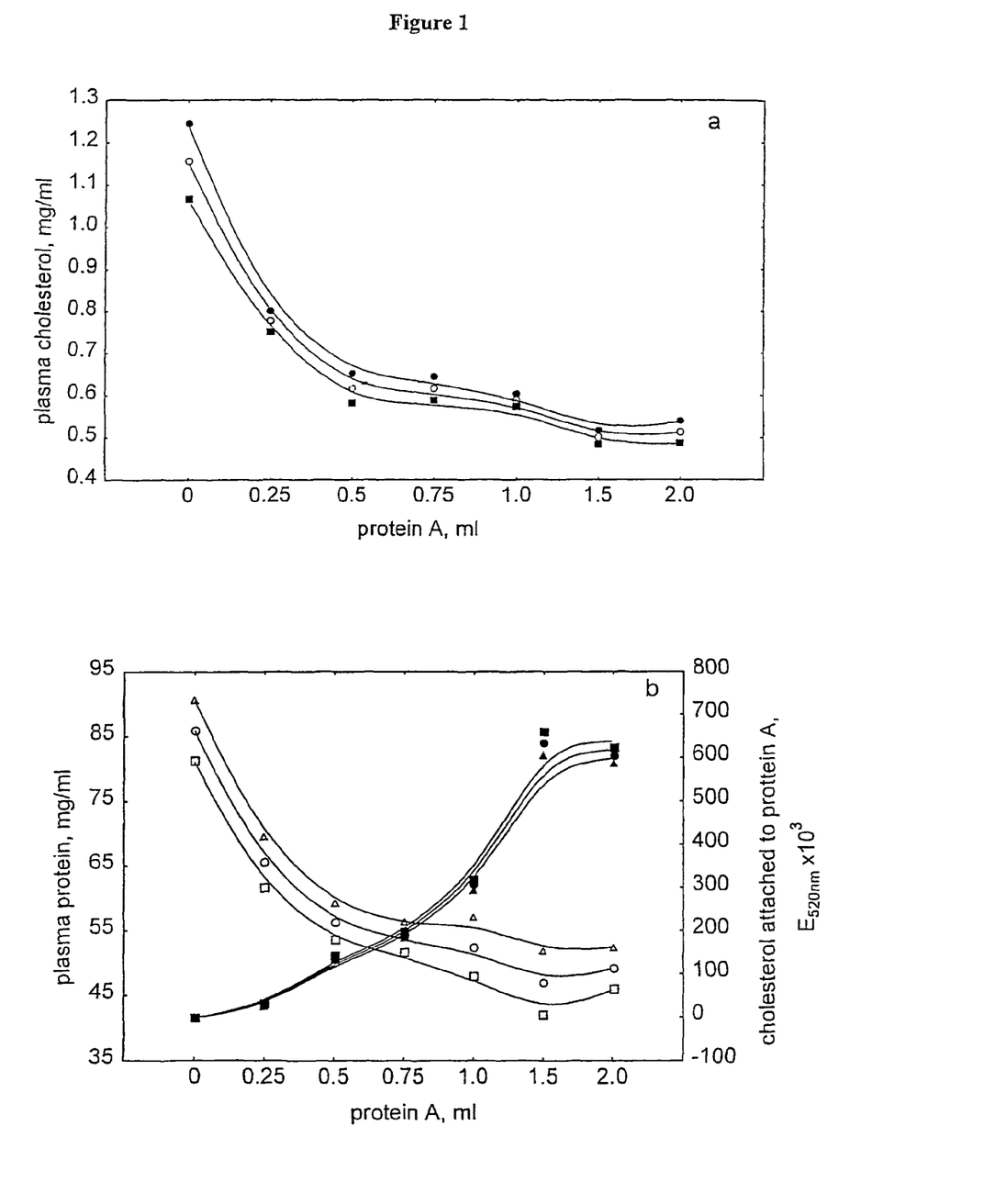
FIG. 1. Titration of protein A with 1 ml of human plasma; results of three experiments with the same sample of donor's plasma are presented; (a) changes of plasma cholesterol; (b) changes of plasma protein, clear points, and level of cholesterol attached to protein A, opaque points; the diluting effect of the added suspension of protein A was taken into account when the calculations of the concentrations were made for this graph.

The results of the titration of protein A reagent with human plasma are presented in FIG. 1. The reduction of cholesterol concentration in the plasma reached its plateau at the same time as the level of cholesterol reached its saturation on the sorbent. This coincided with the exhaustion of the plasma in protein A susceptible immunoglobulins. The maximum of ALICs extraction was achieved when the ratio of the sorbent to plasma was 1.5:1.0.

The process of coagulation consumes not only protein components of plasma but apparently some lipoproteins as well. This is reflected by the fact that the level of cholesterol in sera was always lower (sometimes more than 30%) than its level in the samples of plasma from which they were derived, see Table 1 below. This is supported by another experiment (details of which are not presented in this paper) where the amount of cholesterol attached to the fibrin was between 3.3 and 12.1 μg per mg of the mass of this protein.

TABLE 1

Comparison of the protein and cholesterol extraction by protein A from the plasma and sera of individual patients; the ratio of the volume of the plasma/serum to the volume of protein A was 1:1.5; mean data of three parallel measurements are presented.

| Samples | Protein concentration, mg/ml | | Cholesterol concentration, μg/ml | |
| --- | --- | --- | --- | --- |
| | initial level | after the addition of protein A | initial level | after the addition of protein A |
| Patient No. 1 | | | | |
| Plasma | 88.8 | 45.7 | 1592 | 660 |
| Serum | 73.2 | 37.8 | 1074 | 482 |
| Patient No. 2 | | | | |
| Plasma | 90.4 | 42.5 | 1474 | 678 |
| Serum | 76.8 | 38.4 | 1284 | 458 |
| Patient No. 3 | | | | |
| Plasma | 80.6 | 46.3 | 1294 | 602 |
| Serum | 75.4 | 46.2 | 1208 | 562 |

Apparently for patients No.2 and No.3 coagulation did not consume lipoprotein fraction extractable by protein A, since the level of cholesterol depletion was almost the same in the plasma samples as in the sera. However in the plasma of patient No.3 37% of ALICs were trapped/involved in the process of its coagulation. Therefore, in order to guarantee the full extraction of this type of immune complexes plasma rather than serum is preferably used.

The level of the protein extractable by protein A was about 50% of the total protein of the analysed samples of plasma/serum. The level of lipoproteins, in terms of cholesterol concentration, which were able to interact with this sorbent was between 54-64%. Since this fraction of lipoproteins can interact with protein A only via immunoglobulins associated with them, see Table 2 below, this percentage reflects the level of ALICs in these samples.

Table 2. Demonstration of the immunoglobulin-mediated nature of lipoprotein binding to protein A; *1% TRITON X-100 homogenate of human aortic advanced atheroma; human proteins; *the additional absorption due to the cholesterol of these cells themselves was deducted.

TABLE 2

Demonstration of the immunoglobulin-mediated nature of lipoprotein binding to protein A

| Samples | Cholesterol attached to the sorbent, in $E_{\lambda 520 \, nm} \times 10^3$, after addition of: | |
|---|---|---|
| | 0.5 ml plasma | 0.5 ml homogenate* |
| 0.75 ml 4% agarose | 4 ± 1.5 | 12 ± 2.3 |
| 0.75 ml cross-linked 4% beaded agarose | 0 ± 2.2 | 5 ± 3.5 |
| 0.75 ml protein A conjugated with 4% beaded agarose | 107 ± 5.4 | 266 ± 14.1 |
| 0.75 ml protein A conjugated with 4% beaded agarose + 20 mg IgG** | 3 ± 0.9 | 15 ± 2.7 |
| 0.75 ml protein A conjugated with 4% beaded agarose + 200 mg HSA** | 109 ± 4.1 | 274 ± 11.6 |
| 0.75 ml 10% suspension of bearing protein A *S. aureus* (Cowan strain) | 112 ± 9.3*** | 305 ± 22.1*** |
| 0.75 ml 10% suspension of non-bearing protein A *S. aureus* (Wood 46 strain) | 0 ± 5.5*** | 7 ± 4.8*** |

*1% Triton X-100 homogenate of human aortic advanced atheroma;
**human proteins;
***the additional absorption due to the cholesterol of these cells themselves was deducted.

Example 2

Specificity of the Binding of ALICs with Protein A Reagent

The specificity of the binding of lipoproteins with the protein A reagent and the almost mandatory mediator role in this of immunoglobulins was demonstrated in three experiments. In the first experiment it was shown that the level of cholesterol attached to the 4% agarose itself was 3.7% for the plasma and 4.5% for the aorta homogenate in comparison with the level of the binding towards the full reagent with protein A. When the cross-linked 4% beaded agarose was tested the cholesterol attachment was either non-detectable for plasma or 1.9% for homogenate samples (Table 2).

The necessity of protein A for binding of lipoproteins was supported by another experiment using the Wood 46 strain of Staphylococcus Aureus, which is defective in the expression of protein A. This strain failed to attract any cholesterol in a striking contrast with the Cowan strain bearing protein A.

In the final experiment the incubation of protein A reagent with human IgG prior to the addition to either samples of plasma or aorta homogenates almost totally cancelled the lipoprotein attachment to this reagent. Human serum albumin in a 10 fold higher dose than IgG did not have any significant effect. Since IgGs are the principle link in the binding of a certain fraction of the lipoproteins of the plasma and homogenates, it is possible to state that the lipoproteins extracted by protein A reagent are antigen components of ALICs.

Example 3

The yield of ALICs from aorta homogenates depended on the way they were prepared (Tables 3,4). In the solution of homogenates prepared without any detergent there were no proteins which either belong to immunoglobulins or be associated with them. A similar degree of saturation by immunoglobulin associated material (IAM) solutions was achieved when 1% of non-ionic detergent TRITON X-100 was used. This concentration of the detergent not only provided extract containing 95% of IAM but also increased the absolute amount of it by 188% (Table 3).

TABLE 3

Effect of a procedure on the yield of immunoglobulins/immune complexes extracted from homogenates of human aortic atheromas

| | Total protein concentration, µg/ml | Immunoglobulins/ immune complexes content or IAM** | |
|---|---|---|---|
| Samples* | | µg/ml | % of the total protein |
| Homogenates prepared in PBS | 250 ± 14.7 (n = 3) | 249 | 99.5 |
| Homogenates prepared with 1% of Triton X-100 | 493 ± 11.8 (n = 3) | 469 | 95.2 |
| Homogenates prepared with 1% of Igepal CA-630 | 1815 ± 172 (n = 6) | 928 | 51.1 |
| Homogenates prepared with 90 Units of collagenase | 2395 ± 255 (n = 34) | 837 | 34.9 |

*the amount of immunoglobulins was estimated as the difference between total protein and the level of the protein remaining in the solution of homogenate after its subsequent treatment with protein A and protein L;
**combined data of all types of atheromas analysed are presented.

TABLE 4

Subsequent use of protein A and protein L for the extraction of antibodies and cholesterol-containing lipid antigen(s) from homogenates of human advanced atheromatous plaques (n = 3); 1 ml of protein A was added to 0.5 ml of homogenate.

| Samples | Protein concentration, µg/ml | Cholesterol concentration, µg/ml |
|---|---|---|
| Homogenisation in PBS Without detergent: | | |
| Before the addition of protein A | 250 ± 14.7 | 60.8 ± 0.71 |
| after the addition of protein A | 84.4 ± 4.79 | 20.7 ± 0.76 |
| after the subsequent addition of protein L | 1.25 ± 0.70 | 4.51 ± 0.61 |
| Homogenisation with 1% of Triton X-100: | | |
| before the addition of protein A | 493 ± 11.8 | 119 ± 2.09 |
| after the addition of protein A | 155 ± 11.4 | 44.9 ± 1.00 |
| after the subsequent addition of protein L | 23.7 ± 4.90 | 11.9 ± 0.61 |

The homogenisation of aorta lesions with 1% of another non-ionic detergent, IGEPAL CA-630, resulted in extracts where only half of the total protein belonged to IAM. However its absolute amount was almost twice as high as for the TRITON X-100. A further increase in the concentration of TRITON X-100 or IGEPAL CA-630 led on the one hand to a higher level of the protein to be recovered, but on the other it started to sharply dilute the lipoprotein component of the extracted immune complexes (data not shown).

Collagenase digestion of the aorta provided the highest amount of protein extraction, but despite this the level of IAM in it was lower than in the experiments with IGEPAL CA-630.

62-66% of ALICs of PBS and 1% TRITON X-100 homogenates contained immunoglobulins able to interact with protein A. Another 27%-28% of Igs were extractable by protein L reagent. The remaining 7-10% of lipoproteins could either be free from immunoglobulins, or associated with Igs which neither protein A nor protein L could precipitate. These calculations are based on the assumption that all the molecules of lipoproteins in the analysed samples are the same size and contain the same amount of cholesterol. Although this assumption does not entirely reflect reality, it nevertheless provides an indication regarding the distribution of ALICs in the analysed samples.

In a separate experiment the use of higher doses of TRITON X-100 or IGEPAL CA-630 for the treatment of the protein A/L plasma and tissue extracts revealed that after this procedure there were no detectable amounts of cholesterol attached to Igs, and, therefore, the antibodies extracted were either against other components of lipoproteins or against conformational epitopes of these molecules.

Example 4

Distribution of ALICs in Atherosclerosis

The analysis of the distribution of ALICs 'inside' one patient with severe clinical complications of atherosclerosis is presented in Table 5. The first group of data concerns the level of these complexes which were able to interact with protein A, in terms of cholesterol per protein of IAM. It was demonstrated that their concentration on the surfaces of the atherosclerotic lesions (PBS exaction) was about 3 fold higher than in the plasma. The level of ALICs on these surfaces, in homogenates of the normal part of the arterial wall and quadriceps femoris muscle was about the same.

TABLE 5

Distribution of anti-lipoprotein immune complexes inside one patient with cardiovascular clinical complication of atherosclerosis

| Samples Taken from patient No. 2 | Anti-lipoprotein immune complexes in terms of μg cholesterol/mg IAM extracted* by: | |
|---|---|---|
| | 200 μl of protein A | subsequent use of 200 μl of protein L |
| 150 μl of plasma | 119/3.375 = 35.3 | 11/0.217 = 50.7 |
| PBS extracts of advanced plaques** | 85/0.842 = 101 | 49/0.252 = 194 |
| 1.0 ml 1% Igepal CA-630 homogenates of: | | |
| Quadriceps femoris muscle | 70/0.870 = 80.5 | 78/0.187 = 417 |
| Part of normal arterial wall of abdominal aorta | 104/1.087 = 99.7 | 103/0.261 = 395 |
| Advanced/soft plaque of abdominal aorta | 1480/1.067 = 1387 | 978/0.199 = 4915 |
| Advanced/partially calcified Plaque of abdominal aorta | 1227/1.927 = 638 | 369/0.304 = 1214 |

*amount of protein eluted by acid buffer pH 2.5 from protein A/protein L after their delipidization;
**mean data of the analysis of two tested plaques.

There were different types of atherosclerotic lesions recovered from this patient. One was well advanced but 'soft', another also very developed, but significantly calcified, i.e. 'harder'. The level of ALICs in the homogenate of the former was 131.9 and in homogenate of the latter 6.4 times higher than in the undamaged tissue of the same aorta.

Since the protein L reagent was subsequently used after the treatment of the samples with protein A, much less of the IAM was recovered. However, it seems that the density of ALICs, which avoided the binding by protein A but, nevertheless, were eventually precipitated by protein L reagent, was noticeably higher than the density of the complexes which were extracted by protein A in the first stage of the samples treatment. This difference in density was especially prominent in the tissue homogenates.

Despite these peculiarities the pattern of the distribution of ALICs, which were able to interact with protein L, was about the same as for the ALICs extracted by protein A. The surface of the atherosclerotic lesions contained about 4 fold more of these complexes than their level in plasma. The concentration of this type of ALICs was 3.1 and 12.4 times higher in the 'hard' and in the 'soft' plaques accordingly than in the normal part of the same aorta.

Example 5

'Matched Paired' Clinical Study

The measurement of anti-lipoprotein immune complexes IgG-based (ALICs-IgG) by our procedure was much more revealing than any published data so far. The total level of these complexes in the sera of the patients was 77.9 [μg cholesterol/mg IgG] against 25.3 [μg cholesterol/mg IgG] in the control group. The upper confident level of this parameter in the control is 29.6 [μg cholesterol/mg IgG]. The level of ALICs-IgG exceeding this threshold was detected in 20 cases out of 23 or in 87% for the patients, and only in 4 cases or in 17% for the control (see Table 6).

A comparison of these IgG data with the measurements of cholesterol (classic risk factor for atherosclerosis) in the same sera showed that 5 people in the patients group and 6 people in the control one had slightly more than 2.0 mg/ml. The mean levels of this parameter in both groups were not statistically different (see table below).

Based on this limited study and on these particular groups of people, it is possible to conclude that the accumulation of ALICs-IgG happens not only in an arterial wall in atherosclerosis but also in the blood stream. It seems that this phenomenon is a highly frequent feature in patients with clinical complications of atherosclerosis (at least much more common than hypocholesterolemia). This would suggest that the increased level of plasma ALICs-IgG can serve as an effective marker for screening, diagnosis and monitoring of atherosclerosis.

TABLE 6

Results from "Matched pairs" clinical study

| Groups | ALICs-IgG, in μg cholesterol per mg IgG | Total cholesterol in μg/ml | Groups | ALICs-IgG, in μg cholesterol per mg IgG | Total cholesterol in μg/ml |
|---|---|---|---|---|---|
| Patients: | | | Control: | | |
| 1) Ki | 27.8 | 1,063 | 1) 1 | 24.8 | 2,074 |
| 2) Pi | 29.7 | 1,402 | 2) 2 | 35.9 | 2,182 |
| 3) Ci | 42.8 | 1,723 | 3) 3 | 21.9 | 1,986 |
| 4) Mi | 48.1 | 2,293 | 4) 4 | 24.4 | 2,002 |
| 5) Chs | 36.8 | 1,686 | 5) 5 | 15.3 | 1,806 |
| 6) Y | 22.1 | 1,782 | 6) 6 | 33.1 | 2,038 |
| 7) Ba | 53.6 | 1,438 | 7) 7 | 28.9 | 2,110 |
| 8) Yk | 158.2 | 2,197 | 8) 8 | 22.1 | 1,902 |
| 9) O | 31.7 | 1,543 | 9) 9 | 19.4 | 1,756 |
| 10) M | 20.3 | 1,519 | 10) 10 | 22.5 | 1,638 |
| 11) Sh | 132.3 | 2,002 | 11) 11 | 28.9 | 1,591 |
| 12) Pa | 178.6 | 1,199 | 12) 12 | 24.3 | 1,704 |
| 13) D | 119.0 | 1,015 | 13) 13 | 28.2 | 1,337 |
| 14) Ch | 355.1 | 2,129 | 14) 14 | 28.5 | 1,932 |
| 15) K | 57.7 | 1,223 | 15) 1a | 16.4 | 1,359 |
| 16) C | 29.6 | 1,572 | 16) 2a | 24.9 | 1,607 |
| 17) Z | 36.9 | 1,754 | 17) 3a | 52.5 | 1,714 |
| 18) G | 43.4 | 1,551 | 18) 4a | 27.0 | 1,510 |
| 19) B | 43.2 | 1,693 | 19) 5a | 23.3 | 1,516 |
| 20) A1 | 186.9 | 1,750 | 20) 6a | 20.1 | 1,475 |
| 21) A2 | 55.5 | 1,601 | 21) 7a | 19.8 | 1,480 |

TABLE 6-continued

Results from "Matched pairs" clinical study

| Groups | ALICs-IgG, in µg cholesterol per mg IgG | Total cholesterol in µg/ml | Groups | ALICs-IgG, in µg cholesterol per mg IgG | Total cholesterol in µg/ml |
|---|---|---|---|---|---|
| 22) 40i | 37.4 | 1,286 | 22) 8a | 30.0 | 1,592 |
| 23) 60a | 45.4 | 2,122 | 23) 9a | 8.8 | 2,030 |

Example 6

'Non Match Paired' Norwegian Clinical Study

Figure 2:
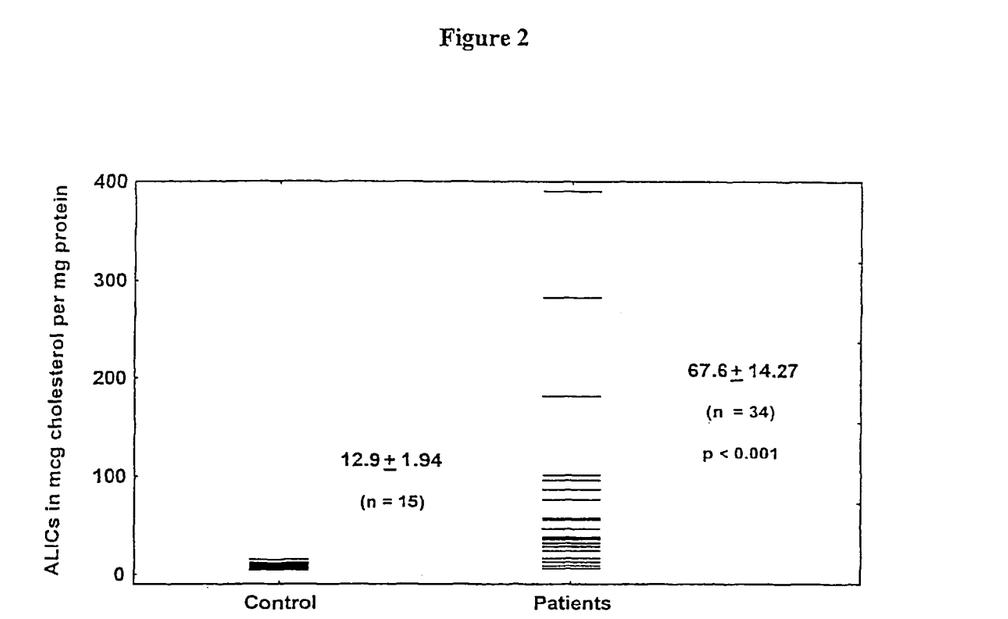
FIG. 2. Comparison of ALICs in μg per mg protein in control and patient group serum samples.

The ages, serum cholesterol, protein and ALICs content of the patient and control groups, plus changes in serum cholesterol and protein concentrations after treatment with protein A, are presented in table 7. The level of ALICs-IgG in the sera of patients was 67.6±1.94 [µg cholesterol/mg protein] compared to 12.9±1.94 in the control group (FIG. 2). This comparison shows that the level of ALICs was more than 5 fold higher in the patient sera than in the healthy control ($p<0.001$).

Figure 3:
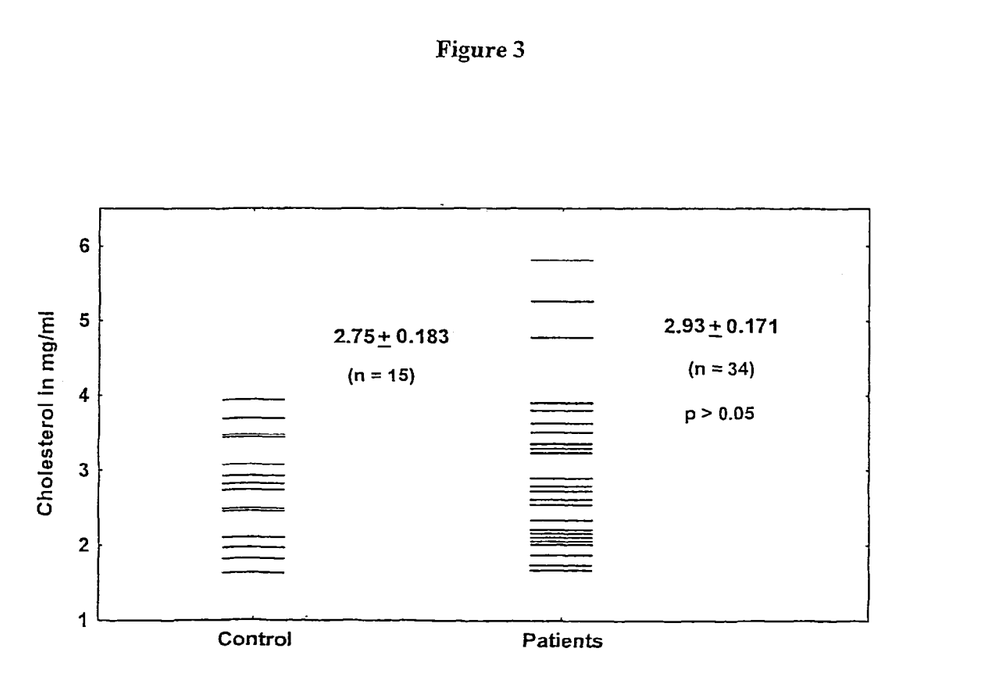
FIG. 3. Comparison of cholesterol in mg/ml in control and patient group serum samples.
Figure 4:
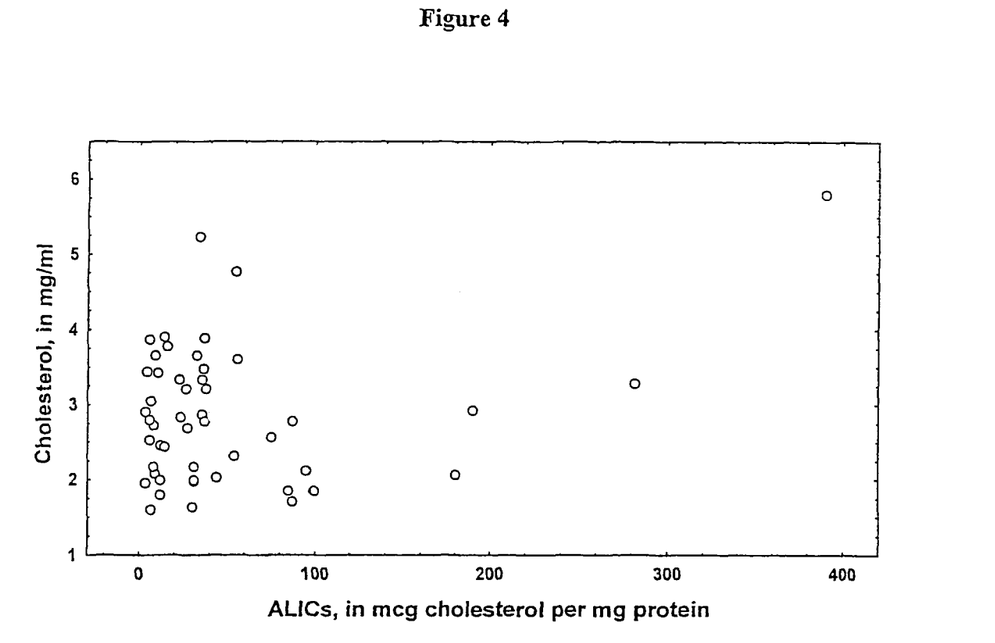
FIG. 4. Correlation between ALICs and cholesterol levels in human sera.
Figure 5:
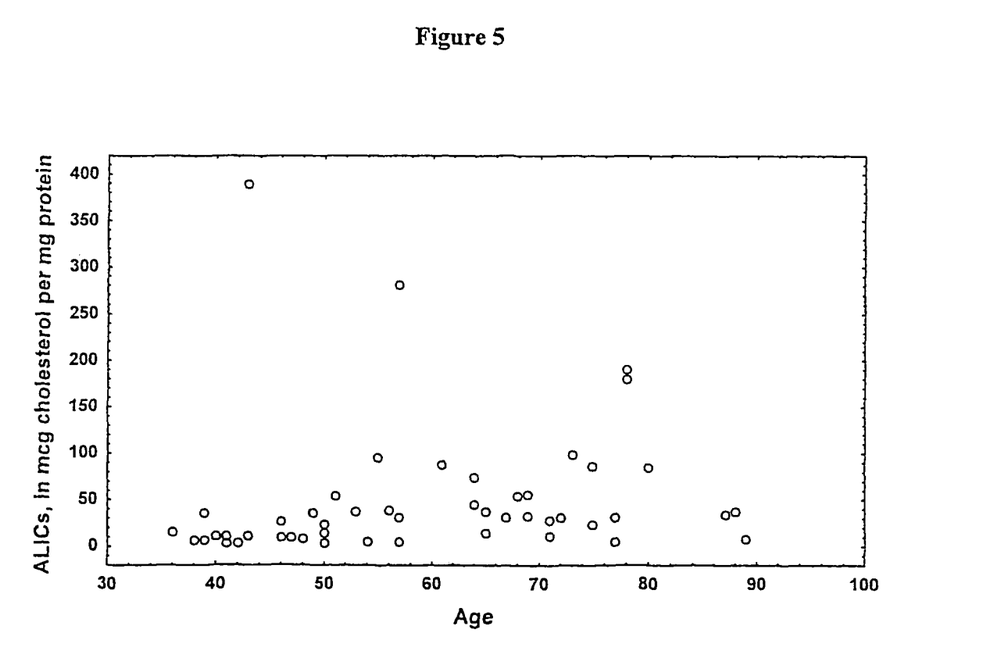
FIG. 5. Correlation between ALICs level and age.

At the same time, the level of cholesterol in both groups was about the same: 2.75±0.183 [mg/ml] for the control group and 2.93±0.171 for the patient group (FIG. 3). A cholesterol level of more than 2.6 mg/ml was found in 52% (18 out of 34) of the patient sera and in 53% (8 out of 15) of the control samples. A correlation analysis showed that the ALICs content is an independent parameter ($r=0.36486$) to cholesterol concentrations in human sera (FIG. 4), and like the latter, is not dependent on the age of the patient (FIG. 5).

An elevated level of ALICs ($\geq 28$ µg cholesterol per mg protein) was found in 76.5% of analysed patient sera and only in 13% of the control samples. These results are similar to those obtained in trials undertaken in the UK and Russia (see table 8, below). A distribution analysis of the control groups from all the clinical studies showed that there were two relatively condensed clusters. One was between 2 and 12 µg cholesterol per mg protein, the other was between 14 and 24 µg cholesterol per mg protein. Presumably their existence corresponds to two different states of the relationships between lipoprotein metabolism and the immune system.

These results demonstrate a significant diagnostic value of ALICs as a specific marker of atherosclerosis. They also confirm that a measurement of cholesterol content provides no useful diagnostic information, which corresponds to the results of many other trials and the practical experience of cardiovascular clinics. 12 samples out of 66 in the control groups had a value outside the upper cluster ($\geq 28$ µg cholesterol per mg protein). It is possible that this 18% of apparently healthy individuals already have active atherosclerosis. In this case the measurement of ALICs may help to detect the beginning of the disease before the development of its clinical manifestation.

TABLE 7

Results from "Non matched pairs" clinical study. Δ - an increment/decrease in cholesterol or protein concentrations caused by the treatment of the sera with protein A agarose.

| Serum from: | Age | Changes in the serum cholesterol concentration caused by treatment with protein A, in mg/ml | | | Changes in the serum protein concentration caused by treatment with protein A, in mg/ml | | | ALICs, in µg cholesterol per mg protein |
|---|---|---|---|---|---|---|---|---|
| | | before | After | Δ | before | after | Δ | |
| Control | | | | | | | | |
| 1. | 40 | 1.81 | 1.12 | 0.693 | 99.7 | 37.3 | 62.4 | 11.1 |
| 2. | 38 | 1.62 | 1.22 | 0.393 | 102.3 | 34.0 | 68.3 | 5.75 |
| 3. | 43 | 2.47 | 1.44 | 1.026 | 96.75 | 34.3 | 92.4 | 11.1 |
| 4. | 48 | 2.73 | 1.51 | 1.218 | 202.8 | 48.6 | 154.2 | 7.9 |
| 5. | 46 | 2.09 | 1.50 | 0.592 | 111.5 | 41.4 | 70.1 | 8.45 |
| 6. | 50 | 2.84 | 1.41 | 1.432 | 119.3 | 56.5 | 62.8 | 22.8 |
| 7. | 54 | 2.80 | 2.40 | 0.403 | 126.7 | 50.6 | 76.1 | 5.3 |
| 8. | 41 | 3.45 | 1.86 | 1.588 | 87.5 | 42.0 | 45.5 | 34.9 |
| 9. | 50 | 2.91 | 1.79 | 1.120 | 70.1 | 33.0 | 37.1 | 30.2 |
| 10. | 47 | 3.67 | 2.64 | 1.027 | 137.2 | 17.8 | 119.4 | 8.6 |
| 11. | 42 | 1.96 | 1.81 | 0.151 | 116.4 | 64.5 | 51.9 | 2.9 |
| 12. | 65 | 3.92 | 2.99 | 0.927 | 111.4 | 45.2 | 66.2 | 14.0 |
| 13. | 50 | 2.44 | 1.69 | 0.749 | 100.2 | 46.3 | 53.9 | 13.9 |
| 14. | 41 | 3.43 | 2.41 | 1.019 | 140.0 | 39.6 | 100.4 | 10.1 |
| 15. | 39 | 3.06 | 2.48 | 0.577 | 129.1 | 33.6 | 95.5 | 6.0 |
| Patients | | | | | | | | |
| 1. | 69 | 3.67 | 2.55 | 1.120 | 79.1 | 33.0 | 35.1 | 31.9 |
| 2. | 56 | 3.22 | 1.67 | 1.549 | 78.8 | 37.7 | 41.1 | 37.7 |
| 3. | 57 | 3.28 | 1.66 | 1.616 | 38.8 | 33.05 | 5.75 | 281 |
| 4. | 53 | 3.49 | 2.44 | 1.051 | 67.0 | 37.9 | 29.1 | 36.1 |
| 5. | 39 | 2.87 | 1.94 | 0.930 | 86.8 | 60.15 | 26.65 | 34.9 |
| 6. | 51 | 4.76 | 2.99 | 1.770 | 94.8 | 62.15 | 32.65 | 54.2 |
| 7. | 69 | 3.61 | 2.79 | 0.818 | 67.7 | 52.9 | 14.8 | 55.3 |
| 8. | 43 | 5.80 | 1.17 | 4.629 | 89.1 | 82.4 | 11.9 | 389 |
| 9. | 87 | 5.24 | 3.61 | 1.630 | 89.1 | 40.3 | 48.8 | 33.4 |
| 10. | 65 | 3.90 | 2.61 | 1.288 | 85.9 | 50.7 | 35.2 | 36.6 |
| 11. | 78 | 2.93 | 1.64 | 1.290 | 67.0 | 60.2 | 6.8 | 190 |
| 12. | 49 | 3.34 | 2.81 | 0.525 | 72.2 | 57.4 | 14.8 | 35.45 |
| 13. | 36 | 3.78 | 3.08 | 0.696 | 95.8 | 50.45 | 45.35 | 15.35 |
| 14. | 46 | 3.22 | 2.08 | 1.140 | 92.3 | 47.95 | 44.35 | 25.7 |
| 15. | 57 | 3.87 | 2.51 | 0.361 | 125.8 | 55.0 | 70.8 | 5.1 |
| 16. | 77 | 2.53 | 2.40 | 0.131 | 65.2 | 40.0 | 25.2 | 5.2 |
| 17. | 71 | 4.96 | 2.71 | 2.254 | 128.4 | 45.3 | 83.1 | 27.1 |
| 18. | 71 | 2.83 | 1.99 | 0.839 | 110.9 | 35.5 | 75.4 | 11.1 |
| 19. | 57 | 3.11 | 1.65 | 1.461 | 102.4 | 54.0 | 48.4 | 30.2 |
| 20. | 89 | 2.61 | 2.19 | 0.419 | 91.3 | 41.9 | 49.5 | 7.30 |
| 21. | 77 | 2.61 | 1.89 | 0.712 | 80.2 | 57.1 | 23.1 | 30.8 |
| 22. | 75 | 5.29 | 3.22 | 2.062 | 133.2 | 40.3 | 92.9 | 22.3 |
| 23. | 55 | 3.29 | 2.13 | 1.125 | 118.2 | 106.3 | 11.9 | 94.5 |
| 24. | 64 | 3.68 | 2.03 | 1.654 | 83.0 | 45.5 | 37.5 | 44.1 |
| 25. | 78 | 3.16 | 2.08 | 1.078 | 61.8 | 55.8 | 6.0 | 180 |
| 26. | 64 | 3.91 | 2.58 | 1.327 | 64.8 | 46.9 | 17.9 | 74.1 |
| 27. | 80 | 3.43 | 1.85 | 1.583 | 78.4 | 59.6 | 18.8 | 84.2 |
| 28. | 73 | 2.96 | 1.86 | 1.097 | 58.4 | 47.3 | 11.1 | 98.8 |
| 29. | 61 | 3.48 | 1.71 | 1.768 | 62.7 | 48.1 | 14.6 | 86.8 |
| 30. | 68 | 3.73 | 2.32 | 1.411 | 61.1 | 34.8 | 26.3 | 53.7 |
| 31. | 75 | 4.43 | 2.78 | 1.654 | 65.9 | 46.8 | 19.1 | 86.6 |
| 32. | 88 | 3.76 | 2.78 | 0.977 | 77.5 | 51.0 | 26.5 | 36.9 |
| 33. | 72 | 3.16 | 1.98 | 1.173 | 74.3 | 36.5 | 37.8 | 31.0 |
| 34. | 67 | 3.28 | 2.01 | 1.275 | 87.5 | 46.0 | 41.5 | 30.7 |

TABLE 8

Comparison of studies in UK, Russia and Norway

| Country | Control | Patients |
|---|---|---|
| | ALICs in µg cholesterol per mg protein | |
| UK | 13.4 ± 2.04 (n = 11) | 84.9 ± 15.3 (n = 28) $p < 0.001$ |

TABLE 8-continued

Comparison of studies in UK, Russia and Norway

| Country | Control | Patients |
|---|---|---|
| Russia | 19.3 ± 1.35 (n = 40) | 61.6 ± 6.50 (n = 46) |
|  |  | p < 0.001 |
| Norway | 12.9 ± 1.94 (n = 15) | 67.6 ± 14.27 (n = 34) |
|  |  | p < 0.001 |
| Total | 16.9 ± 0.99 (n = 66) | 69.5 ± 6.76 (n = 108) |
|  |  | p < 0.001 |

Elevated level of ALICs (≧28 μg cholesterol per mg protein)

| UK | 18% (2 out of 11) | 75.0% (21 out of 28) |
| Russia | 20% (8 out of 40) | 72.5% (35 out of 46) |
| Norway | 13% (2 out of 15) | 76.5% (26 out of 34) |

Example 7
Comparison of measurement of ALICs Using Different Sorbents

These are the results of the study of the comparison of the measuring of ALICs in human sera by using different sorbents. Three procedures were compared:

1) Firstly, 200 μl of serum was treated with 300 μl of a suspension of protein A beaded agarose. The amount of the extracted lipoprotein-immunoglobulin complexes was estimated at this stage. Secondly, 100 μl of the remaining supernatant was treated with 100 μl of a suspension of protein L beaded agarose. The additional amount of lipoprotein-immunoglobulin complexes extracted by this sorbent was also measured.

2) 100 μl of serum was treated with 300 μl of a suspension of protein G beaded agarose.

3) 100 μl of serum was treated with 200 μl of a suspension of a complex of protein A and protein L attached to the beaded agarose.

Results

Whatever the procedure the level of ALICs attached to an immuno-sorbent was always higher in the patient group. The level of ALICs attached to the immune sorbent was measured. See table 9.

An elevated level of ALICs both for the use of just protein A (more than 20 μg, cholesterol per mg of immunoglobulins) and its combination with the sequential use of protein L (more than 60 μg cholesterol per mg of immunoglobulins) was observed in all 17 patients, or in 100%. In the use of the complex sorbent A/L an elevated level of ALICs (more than 30 kg cholesterol per mg of immunoglobulins) was observed in 15 patients out of 17, or in 88%. In the use of the protein G sorbent an elevated level of ALICs (more than 30 μg cholesterol per mg of immunoglobulins) was observed in 11 patients out of 17, or in 65%.

TABLE 9

The comparison of ALICs extraction (in μg cholesterol per mg of immunoglobulins) by different sorbents from the sera of healthy people and patients with clinical complications of atherosclerosis; all measurements were performed in triplicate.

| Tested Groups | Sequence of ALICs exraction by: | | | ALICs extraction by protein G sorbent | ALICs extraction by complex protein A/L sorbent |
|---|---|---|---|---|---|
| | protein A sorbent | by protein L sorbent used subsequently | Total exraction By this double procedure | | |
| Control: | | | | | |
| M  | 20.5 ± 0.54 | 37.9 ± 0.93 | 58.4  | 28.2 ± 0.12 | 29.5 ± 0.23 |
| M3 | 17.1 ± 0.12 | 33.7 ± 0.36 | 50.8  | 17.0 ± 0.65 | 21.6 ± 0.56 |
| K  | 19.5 ± 0.04 | 33.9 ± 0.64 | 53.4  | 18.3 ± 0.32 | 29.0 ± 0.74 |
| K2 | 17.3 ± 0.05 | 34.7 ± 0.16 | 52.0  | 23.2 ± 0.55 | 22.0 ± 0.22 |
| K3 | 19.2 ± 0.27 | 39.5 ± 0.41 | 58.7  | 27.5 ± 0.90 | 25.3 ± 0.71 |
| K4 | 14.7 ± 0.09 | 38.1 ± 0.86 | 52.8  | 21.0 ± 0.46 | 24.4 ± 0.45 |
| K5 | 18.4 ± 1.01 | 31.3 ± 0.55 | 49.7  | 25.9 ± 0.73 | 21.0 ± 0.39 |
| K6 | 18.1 ± 0.08 | 32.8 ± 0.20 | 50.9  | 26.1 ± 1.03 | 22.9 ± 0.30 |
| K7 | 15.9 ± 0.54 | 39.3 ± 0.19 | 55.2  | 16.4 ± 0.44 | 28.9 ± 0.42 |
| K8 | 19.7 ± 0.31 | 20.9 ± 0.83 | 40.6  | 27.8 ± 0.99 | 19.5 ± 0.28 |
| Patients: | | | | | |
| 1  | 20.4 ± 0.68 | 51.0 ± 0.25 | 71.4  | 21.5 ± 0.36 | 32.6 ± 0.26 |
| 5  | 28.0 ± 0.72 | 57.5 ± 0.22 | 85.5  | 35.3 ± 0.95 | 38.1 ± 0.67 |
| 6  | 55.3 ± 1.31 | 42.0 ± 0.54 | 97.3  | 33.0 ± 3.39 | 41.7 ± 0.84 |
| 6a | 38.5 ± 1.37 | 65.5 ± 0.16 | 104.0 | 21.2 ± 0.79 | 24.1 ± 0.52 |
| 7  | 20.8 ± 1.18 | 46.5 ± 0.40 | 67.3  | 20.1 ± 0.78 | 20.6 ± 0.22 |
| 11 | 40.0 ± 3.14 | 37.6 ± 0.58 | 77.6  | 33.1 ± 0.41 | 34.5 ± 0.74 |
| 12 | 52.8 ± 3.12 | 78.4 ± 0.24 | 131.2 | 55.9 ± 0.43 | 60.4 ± 0.33 |
| 13 | 37.3 ± 0.39 | 66.9 ± 1.32 | 104.2 | 39.2 ± 0.64 | 37.6 ± 0.47 |
| 14 | 23.5 ± 0.28 | 59.8 ± 0.96 | 83.3  | 21.5 ± 0.30 | 29.3 ± 0.23 |
| 15 | 23.3 ± 1.06 | 63.8 ± 0.30 | 87.1  | 11.5 ± 0.17 | 33.4 ± 0.40 |
| 16 | 27.5 ± 0.51 | 44.1 ± 1.41 | 71.6  | 28.7 ± 1.26 | 30.3 ± 0.33 |
| 17 | 26.3 ± 1.30 | 63.2 ± 1.62 | 89.5  | 28.9 ± 1.35 | 31.2 ± 0.33 |
| 18 | 40.7 ± 0.81 | 62.9 ± 2.73 | 103.6 | 34.4 ± 1.72 | 34.6 ± 0.18 |
| 19 | 34.0 ± 1.31 | 45.5 ± 0.36 | 79.5  | 36.8 ± 0.83 | 37.7 ± 0.33 |
| 20 | 24.6 ± 0.82 | 57.7 ± 0.81 | 82.3  | 21.9 ± 2.03 | 27.8 ± 0.19 |
| 21 | 35.8 ± 2.44 | 56.1 ± 1.14 | 91.9  | 41.3 ± 0.65 | 37.5 ± 0.73 |
| 22 | 23.2 ± 0.62 | 105.4 ± 1.06 | 128.6 | 35.0 ± 0.90 | 37.7 ± 0.44 |

TABLE 9-continued

The comparison of ALICs extraction (in μg cholesterol per mg of immunoglobulins) by different sorbents from the sera of healthy people and patients with clinical complications of atherosclerosis; all measurements were performed in triplicate.

| Tested Groups | Sequence of ALICs exraction by: | | Total exraction By this double procedure | ALICs extraction by protein G sorbent | ALICs extraction by complex protein A/L sorbent |
|---|---|---|---|---|---|
| | protein A sorbent | by protein L sorbent used subsequently | | | |
| Control | 18.0 ± 0.60 (n = 10) | 34.2 ± 1.54 (n = 10) | 52.3 ± 1.44 (n = 10) | 23.1 ± 1.66 (n = 10) | 24.4 ± 1.26 (n = 10) |
| Patients | 32.5 ± 1.37 (n = 17) | 60.7 ± 1.89 (n = 17) | 91.5 ± 4.44 (n = 17) | 30.5 ± 4.82 (n = 17) | 35.7 ± 2.47 (n = 17) |

Example 8

Outline Protocol for Measurement of ALIC's in a Sample take 100 μl of serum (keep the rest) and add 150 μl of protein A suspension, mix them and keep at 37° C. for 1 hour;

spin the sample at 3,000 g for 10 minutes;

collect and measure the volume of supernatant; it is usually slightly more than the initial 100 μl of the serum, for example, 130 μl, and the degree of the serum dilution would be in this case equal to 1.3;

measure the protein and total cholesterol by any available assay in the sample of the initial serum and in the supernatant; use for the former colorimetric, based on Coomassie blue, micro assay (SIGMA kit 610-A), and for the latter colorimetric enzymatic assay (SIGMA kit 352-20);

after this data measurements for the serum treated with the sorbent should be multiplied by the dilution coefficient, 1.3;

afterwards numbers obtained should be deducted from the same parameters of the untreated serum;

divide the extracted level of cholesterol by the extracted level of protein (immunoglobulins);

the final figures would present the level of ALICs, removed from the serum by immuno-sorbent, in μg cholesterol per mg of immunoglobulins.

The invention claimed is:

1. A method of determining the risk of atherosclerosis in an individual, wherein the method consists essentially of:
   (a) contacting a test blood sample from said individual with an antibody-binding sorbent bound to a solid support and removing from the sample anti-lipoprotein immune complexes bound to the antibody-binding sorbent;
   (b) contacting a control blood sample from a healthy individual with an antibody-binding sorbent bound to a solid support and removing from the sample anti-lipoprotein immune complexes bound to the antibody-binding sorbent;
   (c) measuring the level of cholesterol or lipoprotein associated with said anti-lipoprotein immune complexes from the test sample;
   (d) measuring the level of cholesterol or lipoprotein associated with said anti-lipoprotein immune complexes from the control sample; and
   (e) comparing the level of cholesterol or lipoprotein associated with said anti-lipoprotein immune complexes from the control sample measured in step (d) with the level of cholesterol or lipoprotein associated with said anti-lipoprotein immune complexes from the test sample from the individual measured in step (c);
   wherein an increased level of cholesterol or lipoprotein associated with said anti-lipoprotein immune complexes in the test sample as compared to the control sample from the healthy individual determines increased risk of atherosclerosis in the individual.

2. The method according to claim 1 wherein step (a) consists essentially of contacting the sample with an immunoglobulin binding domain of protein A bound to a solid support.

3. The method according to claim 1 wherein step (a) consists essentially of incubating the sample with antibody-binding sorbent bound to beads to provide a fraction of the sample bound to the beads and an unbound fraction of the sample, and subsequently separating the unbound fraction of the sample from the fraction bound to the beads.

4. The method according to claim 3 wherein the step of separating the unbound fraction from the fraction bound to the beads comprises centrifugation or filtration of the sample.

5. The method according to claim 3 wherein the beads comprise magnetic beads and the step of separating the unbound fraction from the fraction bound to the beads comprises placing the sample in a magnetic field.

6. A method of determining the risk of atherosclerosis in an individual, wherein the method consists essentially of:
   (a) measuring the level of cholesterol or lipoprotein in a test blood sample from said individual;
   (b) measuring the level of cholesterol or lipoprotein in a control blood sample from a healthy individual;
   (c) contacting said test sample with an antibody-binding sorbent bound to a solid support and removing from the sample anti-lipoprotein immune complexes bound to the antibody-binding sorbent;
   (d) contacting said control sample with an antibody-binding sorbent bound to a solid support and removing from the sample anti-lipoprotein immune complexes bound to the antibody-binding sorbent;
   (e) measuring the level of cholesterol or lipoprotein remaining in said test sample after removal of said anti-lipoprotein immune complexes;
   (f) measuring the level of cholesterol or lipoprotein remaining in said control sample after removal of said anti-lipoprotein immune complexes;

(g) determining the level of cholesterol or lipoprotein associated with said removed anti-lipoprotein immune complexes by comparing the level of cholesterol or lipoprotein in the test sample measured in step (a) with the level remaining in step (e);

(h) determining the level of cholesterol or lipoprotein associated with said removed anti-lipoprotein immune complexes by comparing the level of cholesterol or lipoprotein in the control sample measured in step (b) with that remaining in step (f); and (i) comparing the level of cholesterol or lipoprotein associated with said anti-lipoprotein immune complexes from the control sample determined in step (h) with the level of cholesterol or lipoprotein associated with said anti-lipoprotein immune complexes from the test blood sample from the individual determined in step (g);

wherein an increased level of cholesterol or lipoprotein associated with said anti-lipoprotein immune complexes in the test sample as compared to the control sample from the healthy individual determines increased risk of atherosclerosis in the individual.

\* \* \* \* \*